United States Patent [19]
Golds et al.

[11] Patent Number: 6,001,125
[45] Date of Patent: Dec. 14, 1999

[54] PTFE VASCULAR PROSTHESIS AND METHOD OF MANUFACTURE

[75] Inventors: Ellen Golds, Hastings-on-Hudson, N.Y.; David J. Lentz, Andover, Mass.; Jamie Henderson, Oakland; Edward J. Dormier, Rockaway, both of N.J.; Richard J. Zdrahala, Bloomington, Minn.

[73] Assignee: Meadox Medicals, Inc., Oakland, N.J.

[21] Appl. No.: 09/040,880

[22] Filed: Mar. 18, 1998

Related U.S. Application Data

[63] Continuation-in-part of application No. 08/588,052, Jan. 22, 1996, Pat. No. 5,800,512.

[51] Int. Cl.⁶ .................................................. A61F 2/06
[52] U.S. Cl. ............................................ 623/1; 623/12
[58] Field of Search .................... 623/1, 12; 600/36

[56] References Cited

U.S. PATENT DOCUMENTS

| | | |
|---|---|---|
| Re. 31,618 | 7/1984 | Mano et al. . |
| 4,082,893 | 4/1978 | Okita . |
| 4,177,334 | 12/1979 | Okita . |
| 4,250,138 | 2/1981 | Okita . |
| 4,385,093 | 5/1983 | Hubis . |
| 4,478,665 | 10/1984 | Hubis . |
| 4,478,898 | 10/1984 | Kato . |
| 4,482,516 | 11/1984 | Bowman et al. . |
| 4,576,608 | 3/1986 | Homsy . |
| 4,598,011 | 7/1986 | Bowman . |
| 4,743,480 | 5/1988 | Campbell et al. . |
| 4,816,339 | 3/1989 | Tu et al. . |
| 4,857,069 | 8/1989 | Kira . |
| 4,877,661 | 10/1989 | House et al. . |
| 4,925,710 | 5/1990 | Buck et al. . |
| 4,955,899 | 9/1990 | Della Corna et al. . |
| 4,973,609 | 11/1990 | Browne . |
| 5,024,671 | 6/1991 | Tu et al. . |
| 5,026,513 | 6/1991 | House et al. . |
| 5,061,276 | 10/1991 | Tu et al. . |
| 5,123,917 | 6/1992 | Lee . |
| 5,152,782 | 10/1992 | Kowligi et al. . |
| 5,154,866 | 10/1992 | Honda et al. . |
| 5,282,824 | 2/1994 | Gianturco . |
| 5,308,664 | 5/1994 | House et al. . |
| 5,358,678 | 10/1994 | Nakamura et al. . |
| 5,374,473 | 12/1994 | Knox et al. . |

(List continued on next page.)

FOREIGN PATENT DOCUMENTS

| | | |
|---|---|---|
| 716 836 | 6/1996 | European Pat. Off. . |
| 775 472 | 5/1997 | European Pat. Off. . |
| 3-349850 | 12/1991 | Japan . |
| 3-352338 | 12/1991 | Japan . |
| 3-359922 | 12/1991 | Japan . |
| 4-28337 | 2/1992 | Japan . |
| 4-73847 | 3/1992 | Japan . |
| 4-280512 | 9/1992 | Japan . |
| 4-303034 | 12/1992 | Japan . |
| 06343688 | 12/1994 | Japan . |
| 5-321443 | 1/1995 | Japan . |
| 5-243819 | 3/1995 | Japan . |
| WO 95/05132 | 2/1995 | WIPO . |
| WO 95/05277 | 2/1995 | WIPO . |
| WO 95/05555 | 2/1995 | WIPO . |
| WO 95/24304 | 9/1995 | WIPO . |
| WO 96/28115 | 9/1996 | WIPO . |
| WO 98/00090 | 1/1998 | WIPO . |

*Primary Examiner*—Paul J. Hirsch
*Attorney, Agent, or Firm*—Hoffmann & Baron, LLP

[57] ABSTRACT

An implantable microporous ePTFE tubular vascular graft exhibits long term patency, superior radial tensile strength and suture hole elongation resistance. The graft includes a first ePTFE tube and a second ePTFE tube circumferentially disposed over the first tube. The first ePTFE tube exhibits a porosity sufficient to promote cell endothelization tissue ingrowth and healing. The second ePTFE tube exhibits enhanced radial strength in excess of the radial tensile strength of the first tube. The stent provides patency to the endoprosthesis.

14 Claims, 4 Drawing Sheets

U.S. PATENT DOCUMENTS

| | | |
|---|---|---|
| 5,389,106 | 2/1995 | Tower . |
| 5,433,909 | 7/1995 | Martakos et al. . |
| 5,437,900 | 8/1995 | Kuzowski . |
| 5,453,235 | 9/1995 | Calcote et al. . |
| 5,462,781 | 10/1995 | Zukowski . |
| 5,466,509 | 11/1995 | Kowligi et al. . |
| 5,507,771 | 4/1996 | Gianturco . |
| 5,562,697 | 10/1996 | Christiansen . |
| 5,562,728 | 10/1996 | Lazarus et al. . |
| 5,591,195 | 1/1997 | Taheri et al. . |
| 5,620,763 | 4/1997 | House et al. . |
| 5,653,697 | 8/1997 | Quiachon et al. . |
| 5,674,241 | 10/1997 | Bley et al. . |
| 5,700,285 | 12/1997 | Myers et al. . |
| 5,713,917 | 2/1998 | Leonhardt et al. . |
| 5,718,973 | 2/1998 | Lewis et al. . |
| 5,735,892 | 4/1998 | Myers et al. . |
| 5,749,880 | 5/1998 | Banas et al. . |

PTFE VASCULAR PROSTHESIS AND METHOD OF MANUFACTURE

This appln is a CIP of application Ser. No. 08/588,052 filed Jan. 22, 1996 now U.S. Pat. No. 5,800,512.

FIELD OF INVENTION

The present invention relates generally to a tubular implantable prosthesis formed of porous polytetrafluoroethylene. More particularly, the present invention relates to a multi-layered graft/stent endoprosthesis formed of a combination of expanded polytetrafluorethylene, and a tubular diametrically deformable stent

BACKGROUND OF THE INVENTION

It is well known to use extruded tubes of polytetrafluoroethylene (PTFE) as implantable intraluminal prosthesis, particularly vascular grafts. PTFE is particularly suitable as an implantable prosthesis as it exhibits superior biocompatibility. PTFE tubes may be used as vascular grafts in the replacement or repair of a blood vessel as PTFE exhibits low thrombogenicity. In vascular applications, the grafts are manufactured from expanded polytetrafluorethylene (ePTFE) tubes. These tubes have a microporous structure which allows natural tissue ingrowth and cell endothelization once implanted in the vascular system. This contributes to long term healing and patency of the graft.

Grafts formed of ePTFE have a fibrous state which is defined by interspaced nodes interconnected by elongated fibrils. The spaces between the node surfaces that is spanned by the fibrils is defined as the internodal distance (IND). A graft having a large IND enhances tissue ingrowth and cell endothelization as the graft is inherently more porous.

The porosity of an ePTFE vascular graft can be controlled by controlling the IND of the microporous structure of the tube. An increase in the IND within a given structure results in enhanced tissue ingrowth as well as cell endothelization along the inner surface thereof. However, such increase in the porosity of the tubular structure also results in reducing the overall radial tensile strength of the tube as well as reducing the ability for the graft to retain a suture placed therein during implantation. Also, such microporous tubular structures tend to exhibit low axial tear strength, so that a small tear or nick will tend to propagate along the length of the tube.

Attempts to increase the radial tensile, as well as axial tear strength of a microporous ePTFE tube include forming the tubular graft of multiple layers placed over one another. Examples of multi-layered ePTFE tubular structures useful as implantable prostheses are shown in U.S. Pat. Nos. 4,816,338; 4,478,898 and 5,001,276. Other examples of multi-layered structures are shown in Japanese Patent Publication nos. 6-343,688 and 0-022,792.

While each of the above enumerated patents provides tubular graft structures exhibiting enhanced radial tensile strength, as well as enhanced axial tear strength, these structures all result in tubes exhibiting lower porosity. More specifically, the multi-layered ePTFE tubular structures of the prior art exhibit a smaller microporous structure overall, especially at the inner surface, and accordingly, a reduction in the ability of the graft or stent/graft composite to promote endothelization along the inner surface.

Another endoprosthesis commonly used for the treatment of diseases of various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessels. The stent is generally inserted in a radially compressed state and expanded either through a self-expanding mechanism, or through the use of balloon catheters.

A stent may be used in combination with a graft. Such a composite medical device would provide additional support for blood flow through weakened sections of a blood vessel. In endovascular applications the use of stent/graft combinations is becoming increasingly important because the combination not only effectively allows the passage of blood therethrough, but also ensures the implant will remain open.

As may be appreciated with stent/graft configurations, expansion and contraction of the stent exerts a radially tensile force against the graft structure supported thereon. This outward force maintains the stent/graft configuration open once implanted so as to assure patency of the vessel. Where the graft is found having a large IND which enhances tissue ingrowth and cell endothelization, such a graft structure may not possess sufficient strength to retain the expanded stent.

It is therefore desirable to provide an ePTFE vascular graft/stent which exhibits increased porosity especially at the inner surface thereof while retaining a high degree of radial strength especially at the external surface thereof in order to retain the expandable stent.

SUMMARY OF THE INVENTION

It is an object of the present invention to provide an improved ePTFE vascular stent/graft combination.

It is a further object of the present invention to provide a ePTFE vascular stent/graft exhibiting an enhanced microporous structure while retaining superior radial strength provided by a stent, and an outer tear-resistant layer.

It is a still further object of the present invention to provide an ePTFE tubular structure having an inner portion exhibiting enhanced porosity and an outer portion exhibiting enhanced radial tensile strength and suture elongation characteristics.

It is yet another object of the present invention to provide a multi-layered ePTFE tubular vascular stent/graft composite having an inner ePTFE layer which has a porosity sufficient to promote cell endothelization, an intermediate stent layer exhibiting enhanced support strength to maintain patency, and an outer ePTFE layer with enough radial tensile strength to be tear resistant and compatible with said intermediate and inner layer.

In the efficient attainment of these and other objects, the present invention provides a tubular intraluminal prosthesis comprised of a first PTFE tubular structure having a first porosity, a second PTFE tubular structure having a second porosity. The first porosity of said first tubular structure is greater than the second porosity of said second tubular structure. The second PTFE tubular structure is positioned externally about the first PTFE tubular structure. A tubular diametrically deformable stent is interposed between the first and second PTFE tubular structure.

A method of making the tubular intraluminal prosthesis is also disclosed, which comprises the steps of providing a first tubular structure possessing a first porosity, placing a tubular diametrically deformable stent circumferentially around the exterior surface of the first tubular structure, then disposing a second PTFE tubular structure externally about the stent. The second tubular structure should possess a second porosity, such that the first porosity of the first tubular structure is greater than the second porosity of the second tubular structure, and a distinct porosity change between the first and second tubular structures should exist.

DETAILED DESCRIPTION OF THE PREFERRED EMBODIMENTS

The prosthesis of the preferred embodiments of the present invention is a multi-layered tubular structure which is particularly suited for use as an endoprosthesis or vascular graft. The prosthesis is formed of extruded polytetrafluoroethylene (PTFE) as PTFE exhibits superior biocompatability. Further, PTFE is particularly suitable for vascular applications as it exhibits low thrombogenicity. Tubes formed of extruded PTFE may be expanded to form ePTFE tubes where the ePTFE tubes have a fibrous state which is defined by elongated fibrils interconnected by spaced apart nodes. Such tubes are said to have a microporous structure, the porosity of which is determined by the distance between the surfaces of the nodes, referred to as the internodal distance (IND). Tubes having a large IND (greater than 40 microns) generally exhibit long term patency as the larger pores promote cell endothelization along the inner blood contacting surface. Tubes having lower IND (less than 40 microns) exhibit inferior healing characteristics, however they offer superior radial tensile and suture retention strengths desirable in a vascular graft. The present invention provides a composite tubular structure which promotes long term patency of the graft by providing for enhanced cell endothelization along the inner surface while exhibiting enhanced strength due to the presence of the outer layer.

Figure 1:
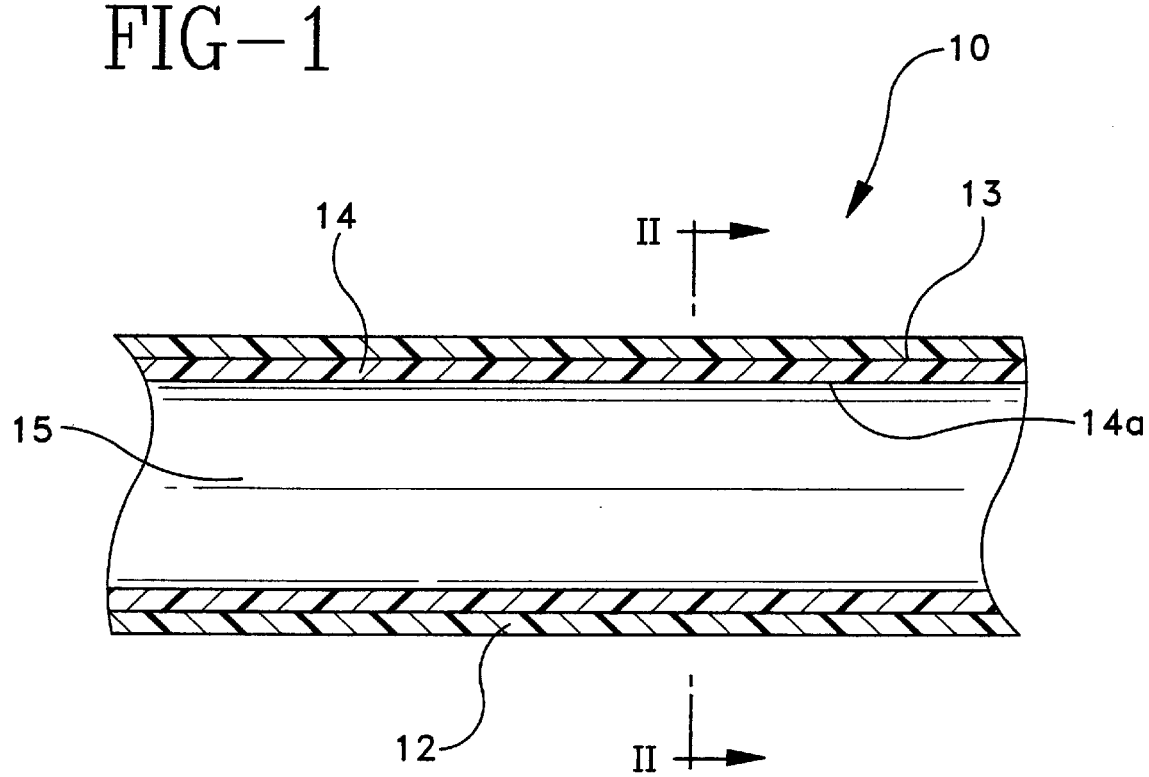
FIG. 1 is a schematic longitudinal cross-section of a multi-layer ePTFE vascular graft of the present invention.
Figure 2:
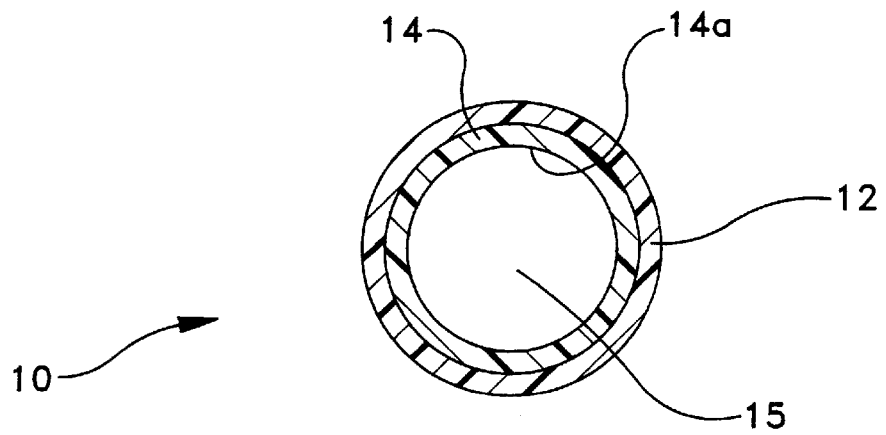
FIG. 2 is a longitudinal cross-section of an alternate embodiment of the present invention producing a multi-layer ePTFE vascular graft.

Referring to FIGS. 1 and 2 of the drawings, composite graft 10 of the present invention is shown. Graft 10 is a elongate tubular structure formed of PTFE. Graft 10 includes a pair of coaxially disposed ePTFE tubes 12 and 14, tube 12 being the outer tube and tube 14 being the inner tube. A central lumen 15 extends through composite graft 10, defined further by the inner wall 14a of inner tube 14, which permits the passage of blood through graft 10 once the graft is properly implanted in the vascular system.

Each tube 12 and 14 may be formed in a separate extrusion process. The process for the paste extrusion of PTFE tubes is well known in the extrusion art. Once extruded, the tubes are expanded to form ePTFE tubes. As will be described hereinbelow, the tubes are expanded using differing process parameters (rates, deformation levels, temperatures, etc) to develop the desired microporous structures. The specifically designed structure of the resulting composite tube has defined properties of strength and porosity which yield a graft 10 having long term patency and good healing characteristics as well as superior strength characteristics.

The present invention is designed to produce grafts with substantially different node/fibril structures with respect to the internal and external portions of the graft which are adjacent to the internal and external graft surfaces. As an example, the inner tube 14 is designed to have relatively high IND while the outer tube 12 is designed to have a lower IND. Further, a distinct porosity change is clearly defined at the interface 13 between tubes 12 and 14. The inner tube 14 having a higher IND to allow enhanced cell endothelization, while the outer tube 12 having a lower IND provides superior strength to the overall composite.

Figure 3:
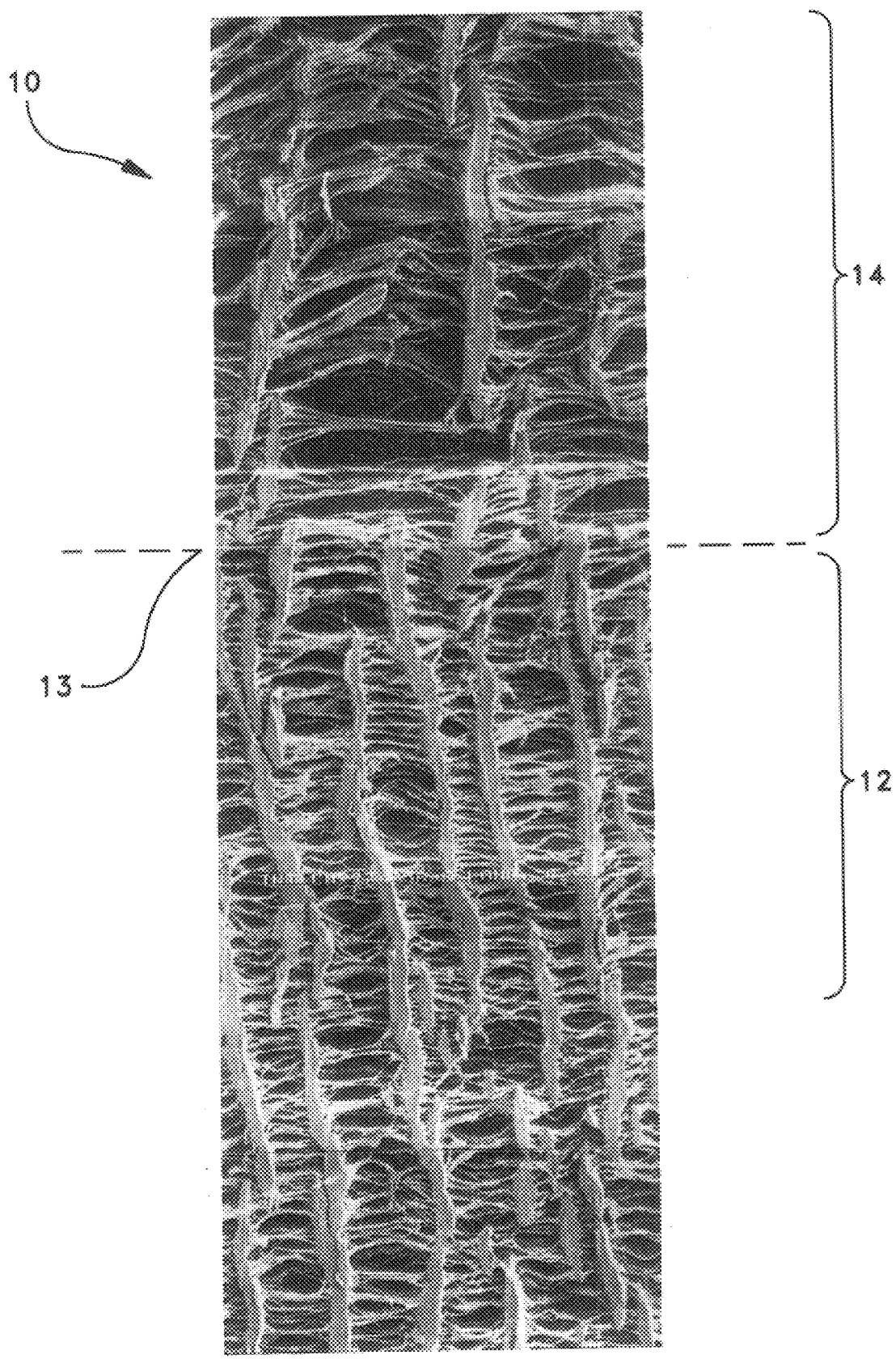
FIG. 3 is a scanning electron micrograph showing a cross-sectional view of a vascular graft produced using the present invention.

An electron micrograph of such a structure produced according to the present invention is shown in FIG. 3. The disparate IND's between the inner tube 14 and outer tube 12 are clearly evident, along with the step change in IND at the interface 13 between the inner tube 14 and outer tube 12. In this example, the strength of the interface 13 has been established by the processing conditions described below to fully adhere the inner tube 14 and outer tube together, hence preventing relative motion and providing enhanced strength.

Graft 10 of the present invention may be formed by expanding a thin wall inner tube 14 at a relatively high degree of elongation, on the order of approximately between 400 and 2000% elongation preferably from about between 700% and 900%. Tube 14 is expanded over a cylindrical mandrel (not shown), such as a stainless steel mandrel at a temperature of between room temperature and 645° F., preferably about 500° F. Tube 14 is preferably but not necessarily fully sintered after expansion. Sintering is typically accomplished at a temperature of between 645° F. and 800° F. preferably at about 660° F. and for a time of between about 5 minutes to 30 minutes, preferably about 15 minutes. The combination of the ePTFE tube 14 over the mandrel is then employed as a second mandrel, over which outer tube 12 is expanded. The ID of the outer tube 12 is selected so that it may be easily but tightly disposed over the OD of inner tube 14. The composite structure 10 is then sintered at preferably similar parameters. The level of elongation of outer tube 12 is lower than that of inner tube 14, approximately between 200% and 500% elongation preferably about 400%. The expansion and sintering of outer tube 12 over the inner tube 14 serves to adheringly bond the interface 13 between the two tubes, resulting in a single composite structure 10.

As shown in FIG. 3, the resulting composite structure has an inner surface defined by inner tube 14 which exhibits an IND of between 40 and 100 microns, spanned by moderate number of fibrils. Such microporous structure is sufficiently large so as to promote enhanced cell endothelization once blood flow is established through graft 10. Such cell endothelization enhances the long term patency of the graft.

The outer structure, defined by outer tube 12, has a smaller microporous structure, with IND of 15–35 microns and a substantial fibril density. Such outer structure results in an increase in the strength of the outer tube, and hence of the composite structure. Importantly, the outer surface defined by the outer tube 12 exhibits enhanced suture retention due to the smaller IND.

Furthermore, the resulting composite structure exhibits a sharp porosity change between the outer tube 12 and inner tube 14. This sharp porosity transition is achieved by providing an inner tube 14 having generally a given uniform porosity therealong and then providing a separate outer tube 14 having a resultant different porosity uniformly therealong. Thus a distinct porosity change is exhibited on either side of the interface 13 defined between inner tube 14 and outer tube 12.

In addition, the forming process described above results in a bonded interface between inner tube 14 and outer tube 12. The interface exhibits sufficient interfacial strength resulting from the direct sintering of the outer tube 12 over the inner tube 14 so as to assure complete bonding of the two tubes. The strength of the interface between the two tubes may be independently varied through selection of processing conditions and relative dimensions of precursor extruded tubes 12 and 14 as desired to yield a range of performance.

The following examples serve to provide further appreciation of the invention but are not meant in any way to restrict the scope of the invention.

EXAMPLE I

A thin extruded tube having wall thickness of 0.41 mm and an inner diameter of 6.2 mm was expanded over a stainless steel mandrel at 500° F. to 900% elongation. The ePTFE tube was then sintered at 660° F. for 14 minutes, cooled, and removed from the oven. A second thin extruded tube having wall thickness of 0.45 mm and an inner diameter of 6.9 mm was expanded over the first tube/mandrel combination at 500° F. and 400% elongation. The composite was then sintered at 660° F. for 14 minutes, cooled and removed from the oven. The resultant composite tube had a wall thickness of 0.65 mm and ID of 5.8 mm.

EXAMPLE II

A thin extruded tube having wall thickness of 0.41 mm and an inner diameter of 6.2 mm was expanded over a stainless steel mandrel at 500° F. to 700% elongation. The ePTFE tube was then sintered at 660° F. for 14 minutes, cooled, and removed from the oven. A second thin extruded tube having wall thickness of 0.45 mm and an inner diameter of 6.9 mm was expanded over the first tube at 500° F. and 400% elongation. The composite was sintered at 660° F. for 14 minutes, cooled, and removed from the oven. The resultant composite tube had a wall thickness of 0.67 mm and an inner diameter of 5.8 mm.

Table I presents physical property data for a vascular graft of the type depicted in Example I described above. The composite graft was removed from the mandrel and subjected to standard testing of radial tensile strength and suture hole elongation. The radial strength of the 900%/400% composite graft is equivalent to a single layer 400% elongation graft and substantially stronger than a single layer 900% elongation graft, despite an overall thinner wall dimension. Additionally, the superior strength of the composite graft is demonstrated by the higher elongation capable of being borne by the graft prior to failure. The lower suture hole elongation, indicative of a smaller tear being caused by suturing and tensioning at a fixed value of 100 grams is clearly demonstrated for the graft prepared by the method of the current invention.

TABLE I

| Physical Property Measurement | 400% Elongation Single Layer Graft | 900%/400% Elongation Composite Graft | 900% Elongation Single Layer Graft |
|---|---|---|---|
| Radial Tensile Strength ($kg/mm^2$) | 0.48 | 0.48 | 0.2 |
| Radial Strain at Break (%) | 550 | 690 | 531 |
| Suture Hole Elongation (%) | 87 | 81 | 158 |
| Wall Thickness | 0.72 | 0.65 | 0.73 |

Figure 4:
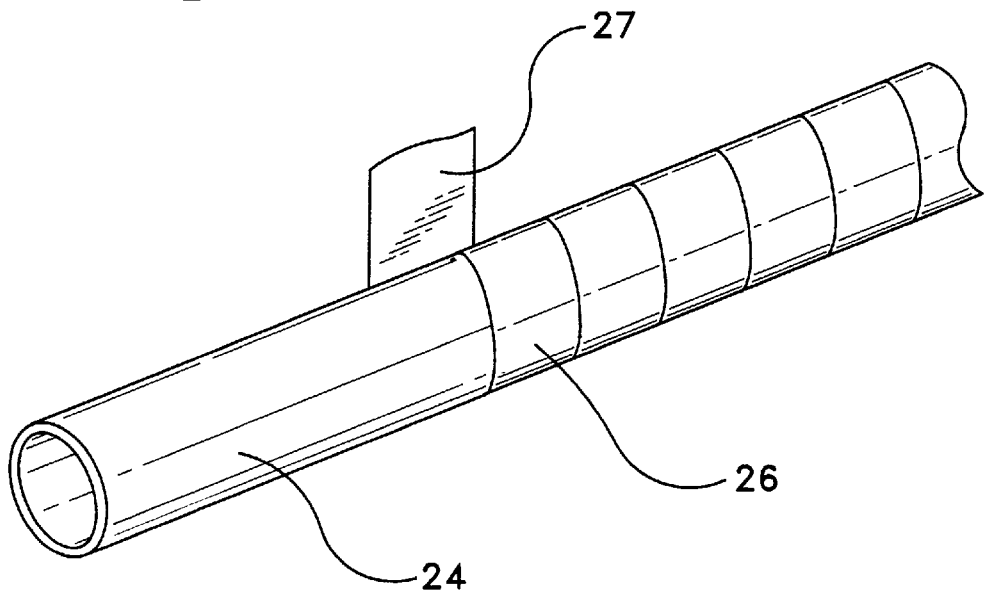
FIG. 4 is a perspective showing of one of the tubular structures of the graft of FIG. 1 over-wrapped with a layer of ePTFE tape.
Figure 5:
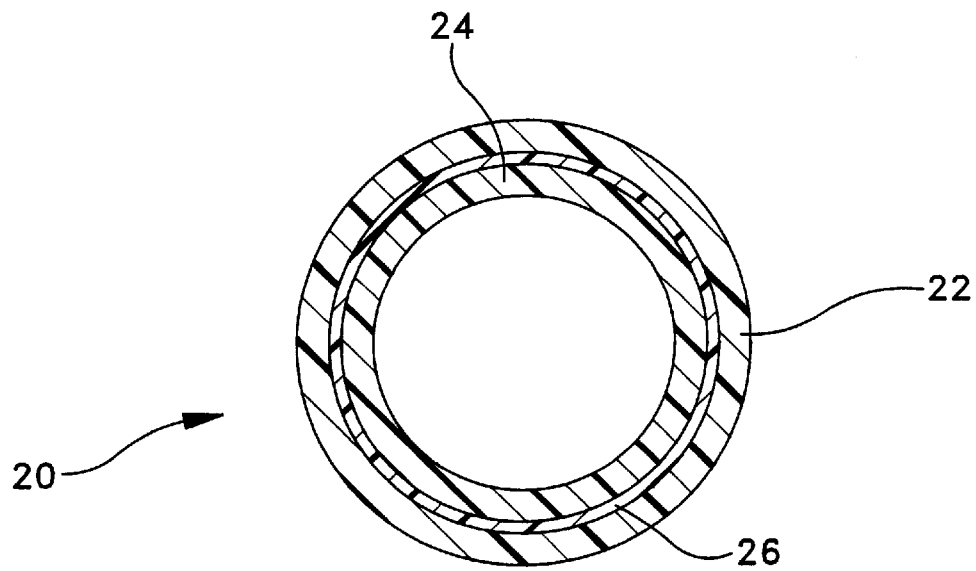
FIG. 5 is a cross-sectional showing of a further embodiment of the ePTFE vascular graft of the present invention.

Referring now to FIGS. 4 and 5, a further embodiment of the present invention is shown. Tubular graft 20 is a composite structure similar to graft 10 described above. Graft 20 includes an outer tube 22 and an inner tube 24 formed generally in the manner described above. In order to further control the porosity and strength of the graft 20, especially at the interface between outer tube 22 and inner tube 24, an additional layer may be employed in combination with outer tube 22 and inner tube 24.

As specifically shown in FIGS. 4 and 5, an additional layer 26 may be employed between inner tube 24 and outer tube 22. Layer 26 may include a helical wrap of ePTFE tape 27 placed over inner tube 24. The additional layer 26, however, may also exist as a sheet, film, yarn, monofilament or multi filament wrap, or additional tube. The additional layer 26 may consist of PTFE, FEP, or other suitable polymer composition to obtain the desired performance characteristics. Layer 26 may be used to impart enhanced properties of porosity and/or strength to the composite graft 20. For example, an additional layer 26 of ePTFE tape 27 having a low IND and wrapped orthogonally to the length direction of graft 20 would increase the radial strength of the resultant composite graft. Similarly, a layer of ePTFE having a high IND would increase the porosity of the composite structure thereby further promoting cell endothelization and/or tissue ingrowth.

As shown in FIG. 4, layer 26 is disposed between inner tube 24 and outer tube 22, and functions as an intermediate layer therein between. It is further contemplated that the additional layer may be employed over outer tube 22, or an additional layer may be used both over outer tube 22 and over inner tube 24.

Figure 8:
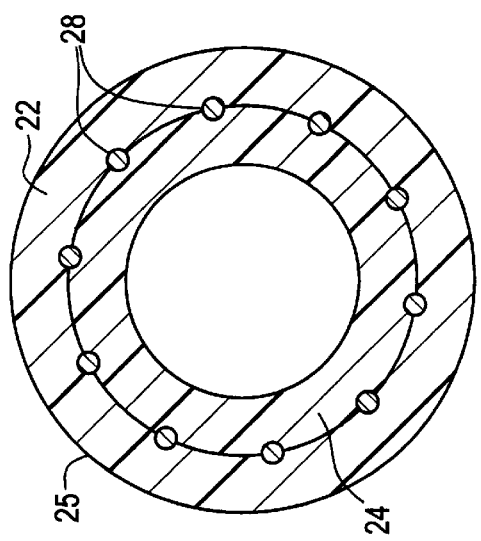
FIG. 8 is a cross-sectional showing of the stent/graft of FIG. 7.
Figure 6:
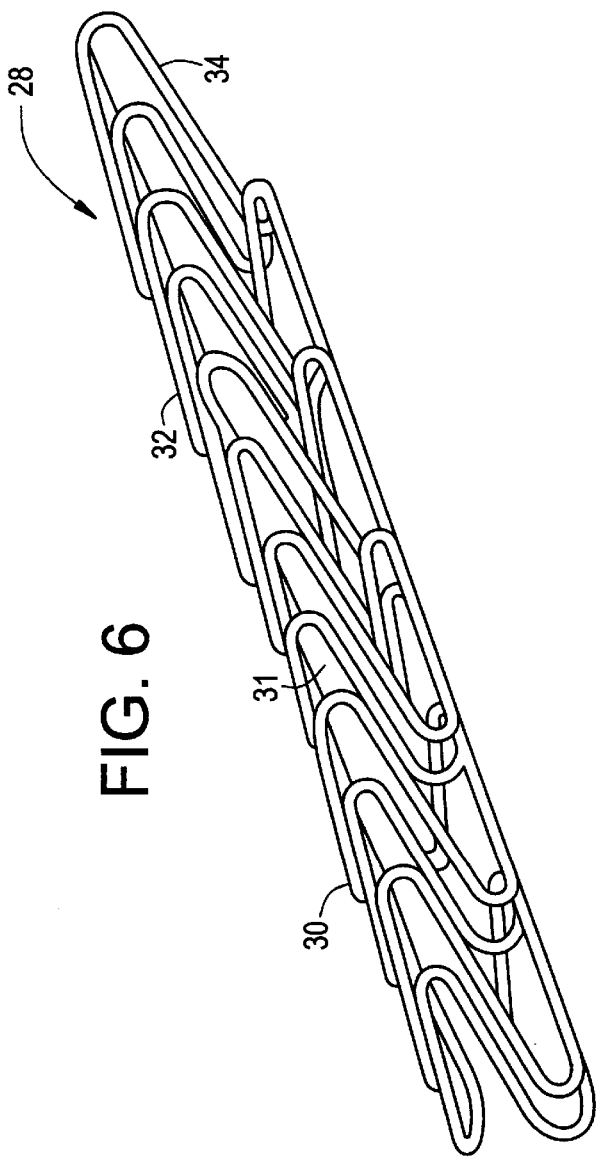
FIG. 6 is a perspective showing a stent which may be used in a composite stent/graft structure of the present invention.
Figure 7:
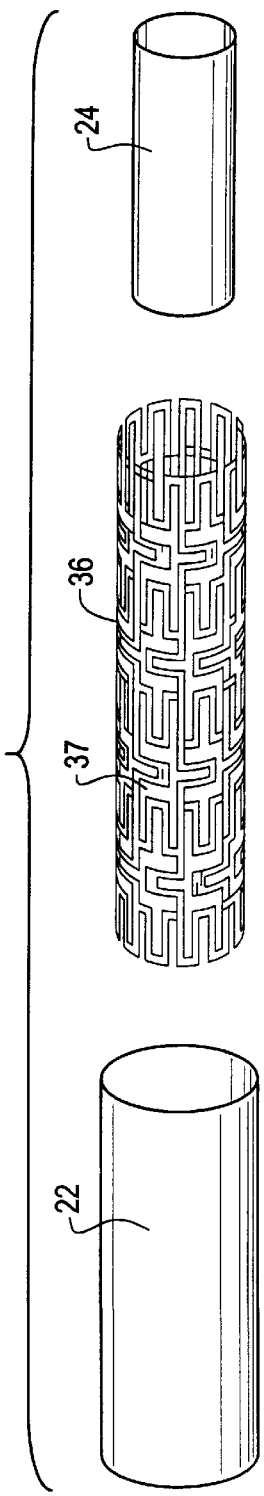
FIG. 7 is an exploded view of the composite stent/graft of the present invention.

With further reference to FIGS. 6–8, a further preferred embodiment of the present invention contemplates placing a stent between the inner tube 24 and outer tube 22, instead of intermediate layer 26 (FIG. 4) so as to form a stent/graft composite device 25. Several advantages exist in employing such a stent/graft composite. The stent provides the prosthesis with significant strength, and ensures patency of the vessel. Furthermore, the stent permits endoluminal dilution as it expands radially outward once implanted. Such expansion is usually accomplished by an expandable balloon of a delivery device. Alternatively, the stent may be of the self-expanding type which expands upon implantation. Such a stent may be formed of a temperature sensing expanding metal such as nitinol.

Although a wide variety of different stents may be used, FIG. 6 shows a perspective view of one particular stent which may be employed between outer tube 22 and inner tube 24.

The particular stent shown in FIG. 7 is more fully described in commonly assigned U.S. Pat. No. 5,575,816 to Rudnick, et al. Stent 28 is an intraluminally implantable stent formed of helically wound wire. Multiple windings 30 of a single metallic wire 32 provide stent 28 with a generally elongate tubular configuration which is radially expandable after implantation in a body vessel. The multiple windings 30 of stent 28 define open spaces 31 through the tubular configuration. Stent 28 further defines a central open passage 34 through the tubular configuration.

Referring to FIG. 7, an exploded view of a stent/graft composite device 25 is shown. Composite device 25 includes an outer tube 22 and inner tube 24 with a stent 36 positioned therebetween. The stent 36 shown in FIG. 7 may be the type more fully described in U.S. Pat. No. 4,733,665, and is an example of another stent configuration which may be employed in the composite stent/graft medical device 25.

Stent 36 is an expandable and deformable tubular structure comprised of longitudinally extending parallel slots 37. The slots define open spaces through the tube. The stent not only ensures patency and flexibility with the slotted configuration, but the open spaces allow adhering of the two tubular layers through the plurality of slots in the stent.

FIG. 8 shows a cross-section of a similar stent/graft composite device where the stent 28 of FIG. 6 is interposed between inner tube 24 and outer tube 22.

While two types of stents are shown herein it is contemplated that a number of different stents may be used in the composite device with one or more inner and outer tubular layers.

In order to make such a composite vascular endoprosthesis, a thin extruded ePTFE tube is taken and expanded over a stainless steel mandrel. The tube 24 is then expanded and sintered in a manner described above. This forms inner tube 24. Stent 28 is then placed over the first tube.

The combination inner tube 24 and stent 28 on the mandrel may then be used as another mandrel over which the outer tubular layer is formed. The inner diameter of the outer tubular layer is selected so that it may be easily but tightly be disposed over the outer diameter of the inner tube and stent. The outer tube 21 may be expanded and sintered in a manner described above.

Adhesive may be used to adhere the stent to the inner tube, the outer tube, or both. Alternatively, the stent may be adhered to the inner and outer tubular layers without the use of an adhesive.

When a stent with a plurality of open spaces or slots therethrough, such as slotted stent 36 or wire stent 28, is utilized in the stent/graft composite device 25, the inner and outer tubular layers may be adhered to each other through the spaces in the stent. Such adherence may be accomplished with the use of an adhesive. Alternatively, the tubular layers may be adhered directly together through the spaces by lamination of the layers. Sintering is one method of effecting such adherence.

Various changes to the foregoing described and shown structures would now be evident to those skilled in the art. Accordingly, the particularly disclosed scope of the invention is set forth in the following claims.

What is claimed is:

1. A tubular intraluminal prosthesis comprising:

a first PTFE tubular structure having a first porosity;

a second PTFE tubular structure having a second porosity less than said first porosity, said second PTFE tubular structure being disposed externally about said first PTFE tubular structure to define a distinct porosity change between said first and second PTFE tubular structure; and a tubular diametrically deformable stent interposed between said first and second PTFE tubular structure.

2. A tubular prosthesis of claim 1 wherein said stent defines a tubular wall having a plurality of open spaces therethrough.

3. A tubular prosthesis of claim 2 wherein said first PTFE tubular structure is adheringly secured to said second PTFE tubular structure through said open spaces of said interposed stent.

4. A tubular prosthesis of claim 2 wherein said tubular wall of said stent includes opposed inner and outer tubular surfaces and wherein said first PTFE tubular structure is adheringly secured to said inner tubular surface of said stent and said second PTFE tubular structure is adheringly secured to said outer tubular surface of said stent.

5. A tubular prosthesis of claim 3 wherein said first PTFE tubular structure is laminated to said second PTFE tubular structure through said open spaces of said interposed stent.

6. A tubular prosthesis of claim 3 wherein said first PTFE tubular structure is adhesively secured to said second PTFE tubular structure through said open spaces of said interposed stent.

7. A tubular prosthesis of claim 4 wherein said first and second PTFE tubular structures are adheringly secured to said inner and outer tubular stent surface by an adhesive.

8. A method of making a tubular intraluminal prosthesis comprising the steps of:

providing a first tubular structure having a first porosity, consisting of an interior and exterior surface;

placing a tubular diametrically deformable stent circumferentially around the exterior surface of said first tubular structure;

disposing a second PTFE tubular structure externally about said tubular diametrically deformable stent, said second PTFE tubular structure having a second porosity less than said first porosity, and defining a distinct porosity change between said first and second PTFE tubular structures.

9. A method of making a tubular intraluminal prosthesis according to claim 8 wherein said stent defines a tubular wall having a plurality of open spaces therethrough.

10. A method of making a tubular intraluminal prosthesis according to claim 9 wherein said first PTFE tubular structure is adheringly secured to said second PTFE tubular structure through said open spaces of said stent.

11. A method of making a tubular prosthesis according to claim 10 wherein said first PTFE tubular structure is laminated to said second PTFE tubular structure through said open spaces of said stent.

12. A method of making a tubular prosthesis according to claim 10 wherein said first PTFE tubular structure is adhesively secured to said second PTFE tubular structure through said open spaces of said stent.

13. A method of making a tubular prosthesis according to claim 8 wherein said tubular wall of said stent includes opposed inner and outer tubular surfaces and wherein said first PTFE tubular structure is adheringly secured to said inner tubular surface of said stent and said second PTFE tubular structure is adheringly secured to said outer tubular surface of said stent.

14. A tubular prosthesis according to claim 13 wherein said first and second PTFE tubular structures are adheringly secured to said inner and outer tubular stent surface by an adhesive.

* * * * *